US006231541B1

(12) United States Patent
Kawamura

(10) Patent No.: US 6,231,541 B1
(45) Date of Patent: May 15, 2001

(54) NO-NEEDLE BLOOD ACCESS DEVICE FOR HEMODIALYSIS AND NO-NEEDLE CONNECTING CANNULA ASSEMBLY

(76) Inventor: Akio Kawamura, 2-75 Tsukisamu-Nishi 2-jo, 10-chome, Toyohira-ku, Sapporo-shi (JP)

( * ) Notice: Subject to any disclaimer, the term of this patent is extended or adjusted under 35 U.S.C. 154(b) by 0 days.

(21) Appl. No.: 09/307,716

(22) Filed: May 10, 1999

(30) Foreign Application Priority Data

Dec. 22, 1998 (JP) ........................................ 10-376402

(51) Int. Cl.[7] ........................................ A61M 11/00

(52) U.S. Cl. .................... 604/93.01; 604/175; 604/6.16; 604/7; 604/507

(58) Field of Search ............................ 604/93.01, 94.01, 604/174, 175, 4, 7, 8, 9, 249, 33

(56) References Cited

U.S. PATENT DOCUMENTS 3,826,257 * 7/1974 Buselmeier ...................... 128/214 R
4,559,039 * 12/1985 Ash et al. ........................... 604/175
4,822,341 * 4/1989 Colone ................................ 604/175

OTHER PUBLICATIONS

A.J. Collins, et al., Blood Access Without Skin Puncture, vol. XXVII Trans Am Soc Artif Inter Organs, 1981, pp. 308–313.

A.A. Kaplan, et al., Regional Experience with the Hemasite™ No–Needle Access Device, vol. XXIX Trans Am Soc Artif Intern Organs 1983, pp. 369–372.

N. Graben, et al., Successful Conversion of External Shunts to Arteriovenous Fistulas in Adults with End–Stage Renal Failure, vol. XXIX Trans Am Soc Artif Intern Organs, 1983, p. 373.

R.H. Barth, et al., High Incidence of Infectious Complications with the Hemasite™ Vascular Access Device, vol. XXX Trans Am Soc Artif Intern Organs, 1984, pp. 450–457.

* cited by examiner

*Primary Examiner*—Richard K. Seidel
*Assistant Examiner*—Jennifer Maynard
(74) *Attorney, Agent, or Firm*—Griffin & Szipl, P.C.

(57) ABSTRACT

A no-needle blood access device for hemodialysis comprising, an artificial conduit (12) whose opposite ends are anastomosed to a targeted artery or vein; a metallic body (20), the body including a cylindrical horizontal portion (22) covering the entire circumference of the conduit or an arcuate-shaped horizontal portion (50) covering at least an upper half of the circumference of the conduit, and a cylindrical vertical portion (24) connected to approximately the center of the upper part of the horizontal portion so as to be disposed perpendicular to the horizontal portion and defining a well (26) therein, the horizontal portion being provided at the part located at the bottom of the well with a first pair of apertures (30, 32), the conduit being provided at the corresponding part with a second pair of apertures (30, 32), whereby the well is in communication with the conduit through the apertures; and a pair of shutters (34, 36) slidably housed within opposed pockets formed in the upper part of the horizontal portion respectively and arranged such that they can be opened and closed; whereby the device is arranged such that, when the shutters are opened, the well is brought into communication with the conduit, and when the shutters are closed, the well is brought out of communication with the conduit.

12 Claims, 11 Drawing Sheets

F I G. 3 A
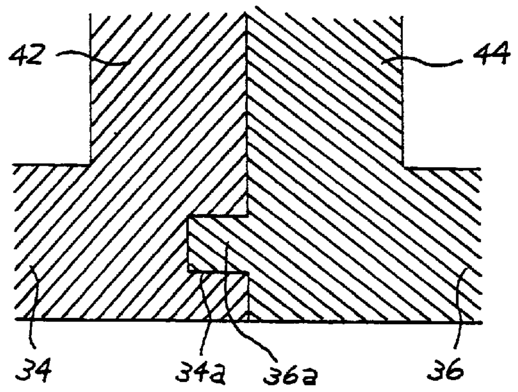
F I G. 3 B
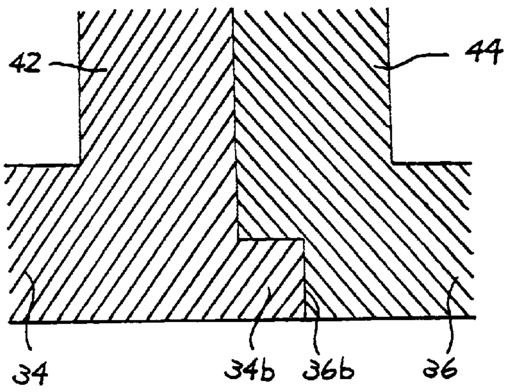

F I G. 7 B
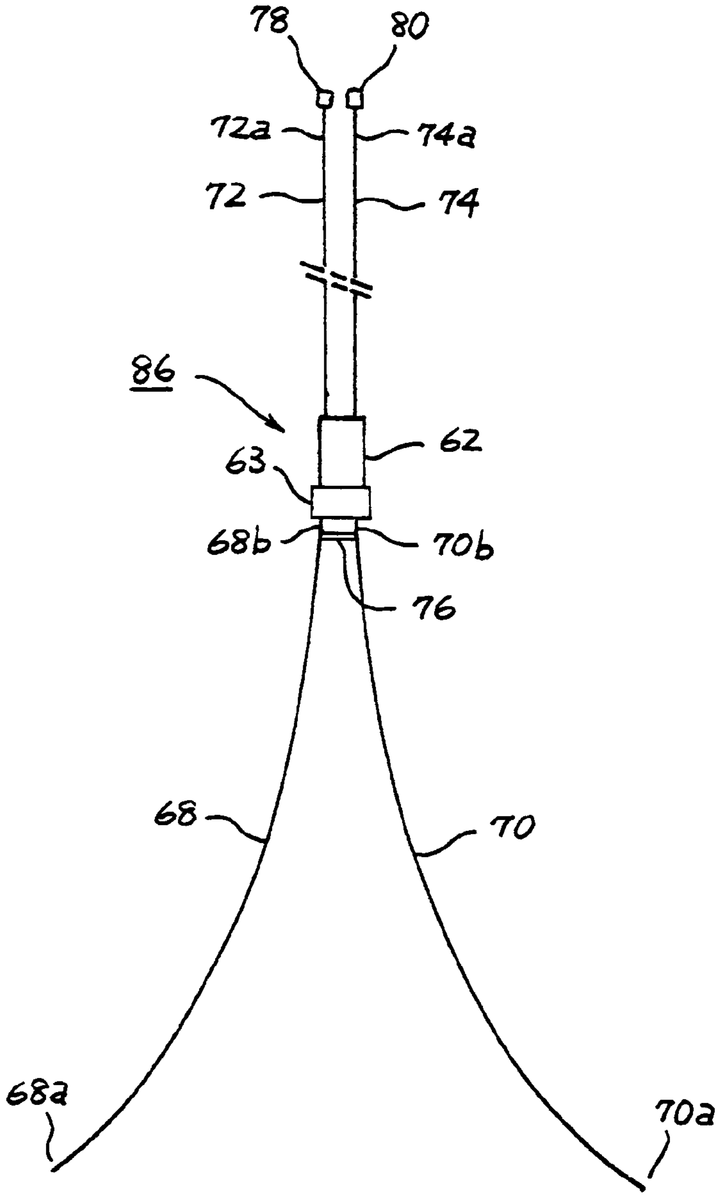

NO-NEEDLE BLOOD ACCESS DEVICE FOR HEMODIALYSIS AND NO-NEEDLE CONNECTING CANNULA ASSEMBLY

BACKGROUND OF THE INVENTION

The present invention generally relates to a no-needle blood access device for hemodialysis and a no-needle connecting cannula assembly. More specifically, the present invention relates to a no-needle blood access device for hemodialysis with a mechanism of simple structure, as well as a no-needle connecting cannula assembly which enables a patient to move around with relative freedom during hemodialysis.

DESCRIPTION OF THE PRIOR ART

Hemodialysis is used widely as a remedy for treating kidney insufficiency. In many cases, a surgical short circuit which is commonly referred to as "shunt" is implanted in a blood vessel or blood vessels of the patient suffering from serious kidney disease, because such a patient must receive hemodialysis treatment periodically over a long period of time. Shunts are divided broadly into two categories, internal shunts and external shunts. The internal shunt has a drawback that needle puncture is required during hemodialysis. On the other hand, the external shunt has a high rate of thrombosis and infection, and makes daily life more inconvenient.

To overcome these drawbacks of the prior shunts, a new blood access device for hemodialysis has been proposed. The blood access device given the tradename "Hemasite" conceptually belongs to the external shunt group. The Hemasite blood access device is equipped with a tool that has a back-flow valve for blood, and is adapted to acquire a plentiful blood flow immediately if the tool is simply connected to a circuit leading to a dialyzer. This Hemasite blood access device has an advantage that needle puncture is not required, but due to its complicated structure, it is costly and troublesome to handle.

On the other hand, presently, a circuit for connecting the blood access devices implanted in human bodies to a dialyzer during hemodialysis consists of tubes each having a relatively large diameter, and each of these tubes is short, because the amount of blood circulating outside the body of the patient has to be reduced so as not to load the human body. This is due to the reason that the amount of blood circulating outside the body of the patient becomes large if the circuit is made of long tubes with a large diameter. Accordingly, if the prior circuit is used to hemodialyze, the patient cannot move about freely and must lie on a bed quietly, during hemodialysis.

SUMMARY OF THE INVENTION

It is therefore an object of the present invention to provide a blood access device for hemodialysis which does not require needle puncture, and which has a mechanism of simple structure, and which can be manufactured at a relatively low cost, and which is easy to handle, as well as a no-needle connecting cannulas assembly which enables a patient to move around with relative freedom during hemodialysis.

The above and other objects of the present invention can be accomplished by a no-needle blood access device for hemodialysis comprising, an artificial conduit whose opposite ends are anastomosed to a targeted artery or vein; a metallic body, the body including a cylindrical horizontal portion covering the entire circumference of the conduit or an arcuate-shaped horizontal portion covering at least an upper half of the circumference of the conduit, and a cylindrical vertical portion connected to approximately the center of the upper part of the horizontal portion so as to be disposed perpendicularly to the horizontal portion and defining a well therein, the horizontal portion being provided at the part located at the bottom of the well with a first pair of apertures, the conduit being provided at the corresponding part with a second pair of apertures, whereby the well is in communication with the conduit through the apertures; and a pair of shutters slidably housed within opposed pockets formed in the upper part of the horizontal portion respectively and arranged such that they can be opened and closed; whereby the device is arranged such that, when the shutters are opened, the well is brought into communication with the conduit, and when the shutters are closed, the well is brought out of communication with the conduit.

Further, the above and other objects of the present invention can be accomplished by a no-needle connecting cannula assembly for hemodialysis comprising, a cap provided with a pair of through-holes; a first pair of cannulas connected to one end of the through-holes respectively so as to be in communication with the corresponding through-holes, the external diameter of the respective leading ends of the cannulas being selected to be slightly smaller than the diameter of the apertures, the external diameter of the respective ends of the side of the cannulas to which the cap is connected being selected to be slightly larger than the diameter of the apertures; and a second pair of cannulas connected to the other end of the through-holes respectively so as to be in communication with the corresponding through-holes and adapted to define a connecting circuit leading to a dialyzer, the second pair of cannulas having an internal diameter approximately equal to the internal diameter of each of the first pair of cannulas, the second pair of cannulas being at least 3 meters in length, one of the second pair of cannulas being provided at an end proximal to the dialyzer with a terminal for connecting to a terminal of the dialyzer, the other of the second pair of cannulas being provided at an end proximal to the dialyzer with a terminal for connecting to a terminal of the dialyzer.

In a preferred aspect of the present invention, each of the shutters of the no-needle blood access device for hemodialysis is provided at their opposite ends with upwardly extending projection pieces, respectively, and the projection pieces serve as a knob during the opening and closing of the shutters.

In another preferred aspect of the present invention, one of the projection pieces of the no-needle blood access device for hemodialysis is formed to be higher than the other.

In a further preferred aspect of the present invention, each of the projection pieces of the no-needle blood access device for hemodialysis is mounted on the shutters, respectively, so that one of the projection piece shifts slightly with respect to the other in a horizontal direction along those ends.

In a further preferred aspect of the present invention, the end of the first shutter of the no-needle blood access device facing the second shutter is provided with a recess or a stepped part, and the end of the second shutter facing the first shutter is provided with a projection or a stepped part adapted to mate with the recess or the stepped part when the shutters are closed.

In a further preferred aspect of the present invention, the first pair of cannulas of the connecting cannula assembly curve so that the curvature becomes larger from the end proximal to the cap towards the end distal to the cap.

In a further preferred aspect of the present invention, the first pair of cannulas of the connecting cannula assembly curve so that the curvature becomes larger from the end proximal to the cap towards the end distal to the cap and intersects at a location adjacent to the end proximal to the cap.

In a further preferred aspect of the present invention, when each of the first pair of cannulas is inserted from the apertures of the body of the blood access devices for hemodialysis through the artificial conduit into the targeted artery or vein, the length of each of the first pair of cannulas of the connecting cannula assembly is selected so that the distance between the anastomosis area of the artificial conduit to the targeted artery or vein and the respective leading ends of the first pair of cannulas is about 3 centimeters.

The above and other objects and features of the present invention will become apparent from the following description made with reference to the accompanying drawings.

BRIEF DESCRIPTION OF THE DRAWINGS

FIG. 3A is an enlarged sectional view of abutting parts of shutters of the no-needle blood access device for hemodialysis of FIG. 1.

FIG. 3B is an enlarged sectional view of another version of abutting parts of shutters of the no-needle blood access device for hemodialysis of FIG. 1.

FIG. 7B is a diagrammatic view of a second embodiment of the no-needle connecting cannula assembly of the present invention.

DESCRIPTION OF THE PREFERRED EMBODIMENTS

Figure 1:
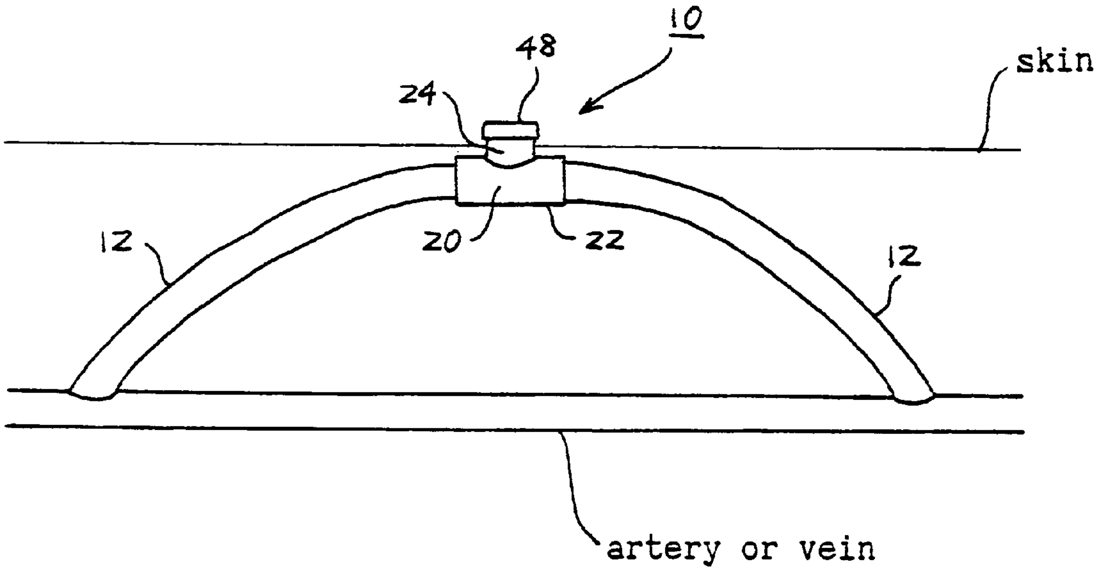
FIG. 1 is a diagrammatic view of a no-needle blood access device for hemodialysis of a preferred embodiment of the present invention which is implanted in a human body.

The preferred embodiments of the present invention will now be explained with reference to the accompanying drawings. A no-needle blood access device for hemodialysis generally indicated by a reference numeral 10 in FIG. 1 which is an embodiment of the present invention comprises a metallic body 20. The body 20 includes a cylindrical horizontal portion 22 and a cylindrical vertical portion 24 connected to approximately the center of the upper part of the horizontal portion 22 so as to be disposed perpendicular to the horizontal portion 22. The vertical portion 24 defines a well 26 therein. The body 20 is generally an inverted T-shape, as viewed from the side, as shown in FIG. 1.

Preferably, the body 20 is made from titanium which is light and biocompatible, and the part of the body 20 with which blood comes into contact is covered with pyrolitic carbon which is an anticoagulant substance. Further, preferably, the external surface of each of the horizontal portion 22 and the vertical portion 24 is covered with a biocompatible fiber 28 such as dacron velour in order to enhance the fusion with human tissue and provide a barrier to bacteria invading from the outside.

An artificial conduit 12 is passed into the horizontal portion 22 of the body 20. The artificial conduit 12 is prevented from moving inside the horizontal portion 22, because the horizontal portion 22 is formed so that the internal diameter is substantially equal to the external diameter of the artificial conduit 12, and adhesive (not shown) is applied on the area between the internal surface of the horizontal portion 22 and the external surface of the artificial conduit 12. The adhesive applied on the area between the internal surface of the horizontal portion 22 and the external surface of the artificial conduit 12 may be biocompatible.

Figure 2:
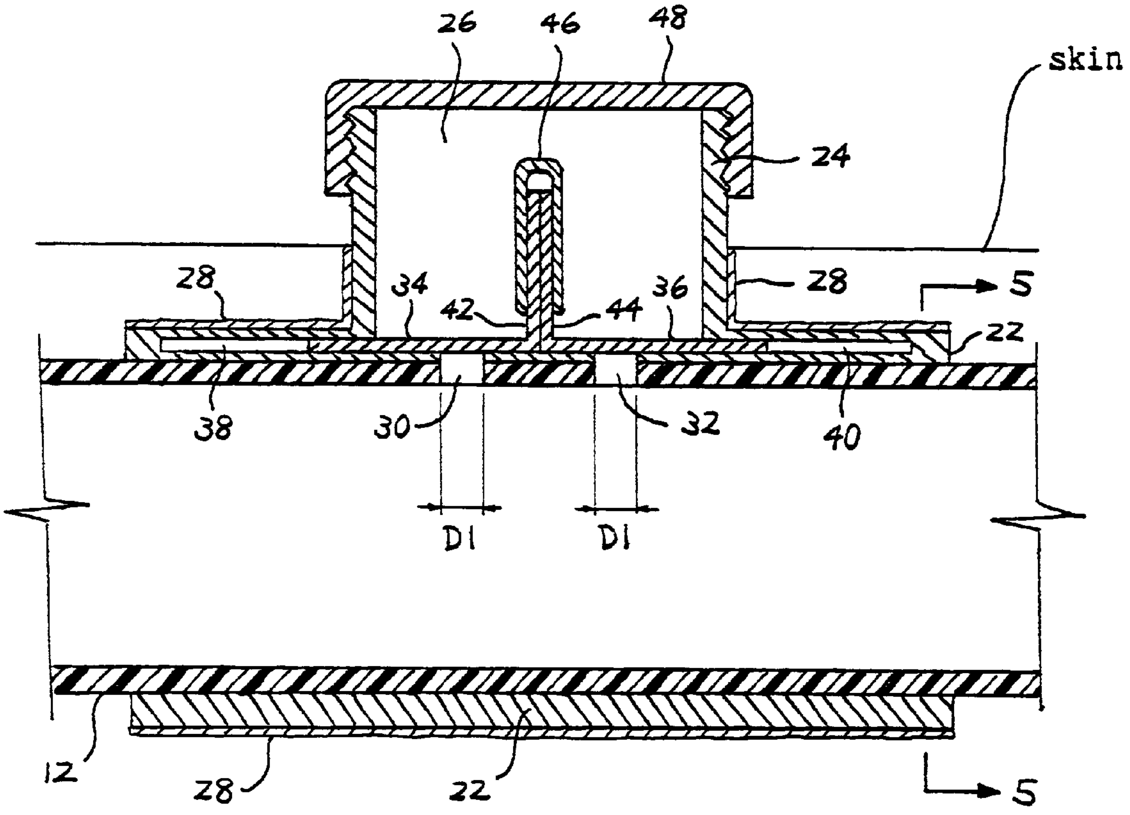
FIG. 2 is an enlarged sectional view of a body of the no-needle blood access device for hemodialysis of FIG. 1.

As best shown in FIG. 2, a pair of apertures 30 and 32, the diameter of each of which is D1 are provided at the part of the horizontal portion 22 located at the bottom of the well 26 and the corresponding part of the artificial conduit 12 respectively, whereby the well 26 is in communication with the artificial conduit 12 through the apertures 30 and 32.

The body 20 further includes a pair of shutters 34 and 36 for bringing the well 26 out of communication with the artificial conduit 12. Each of the shutters 34 and 36 is housed within opposed pockets 38 and 40 formed in the upper part of the horizontal portion 22, respectively, and is arranged such that they can be opened and closed. More specifically, as shown in FIG. 2, the horizontal portion 22 is provided at locations facing the well 26 of the upper part with the pockets or recesses 38 and 40 respectively, and each of the plate-shaped shutters 34 and 36 is received in a sliding manner within the pockets 38 and 40 respectively. Each of the shutters 34 and 36 is provided at their opposite ends with upwardly extending projection pieces 42 and 44 respectively. Each of the projection pieces 42 and 44 serves as a knob during the opening and closing of the shutters 34 and 36. As shown in FIG. 2, the surface of the projection piece 42 facing the projection piece 44 is adapted to abut on the surface of the projection piece 44 facing the projection piece 42 when the shutters 34 and 36 are closed.

Preferably, as shown in FIG. 3A, the end of the shutter 34 facing the shutter 36 is provided with a recess 34*a*, and the end of the shutter 36 facing the shutter 34 is provided with a projection 36*a* which is adapted to mate with the recess 34*a* when the shutters 34 and 36 are closed. Alternatively, instead of the recess 34*a* and the projection 36*a*, as shown in FIG. 3B, the end of the shutter 34 facing the shutter 36 may be provided with a stepped part 34*b*, while the end of the shutter 36 facing the shutter 34 may be provided with a stepped part 36*b* adapted to mate with the stepped part 34*b* when the shutters 34 and 36 are closed. According to the construction, it is possible to bring the well 26 out of communication with the artificial conduit 12 completely when the shutters 34 and 36 are closed.

Figure 4A:
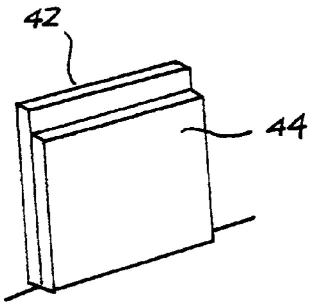
FIG. 4A is a perspective view of projection pieces of the shutters of the blood access device.
Figure 4B:
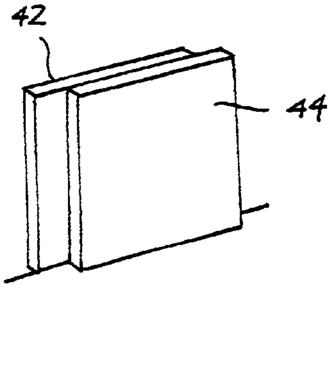
FIG. 4B is a perspective view of another version of projection pieces of the shutters of the blood access device.

FIGS. 4A and 4B show two embodiments of the projection pieces 42 and 44. In the embodiment shown in FIG. 4A, the projection piece 42 is formed to be higher than the projection piece 44. On the other hand, in the embodiment shown in FIG. 4B, each of the projection pieces 42 and 44 are mounted on the shutters 34 and 36 respectively so that the projection piece 42 shifts slightly with respect to the projection piece 44 in a horizontal direction along those ends. Alternatively, one projection piece (not shown) may be formed so that the width is larger than that of the other projection piece(not shown). According to these constructions, when the shutters 34 and 36 are to be opened and closed by a tool such as a pincette, it is easy to grasp them with the tool.

As shown in FIG. 2, the projection pieces 42 and 44 may be secured with respect to each other by a clip 46 to prevent the shutters 34 and 36 from opening when they are closed. Further, the top of the vertical portion 24 may be covered with a cap 48 to cover up the well 26 when the blood access device 10 is not in use.

Figure 5:
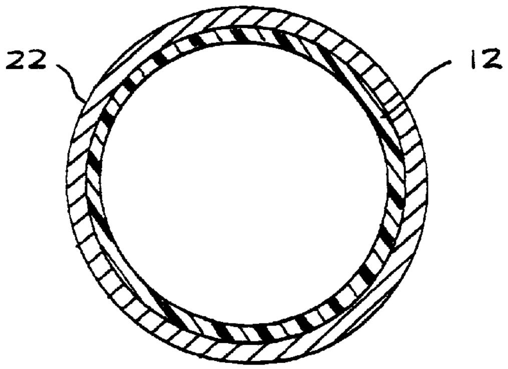
FIG. 5 is a cross sectional view taken along line 5—5 in FIG. 2.
Figure 6:
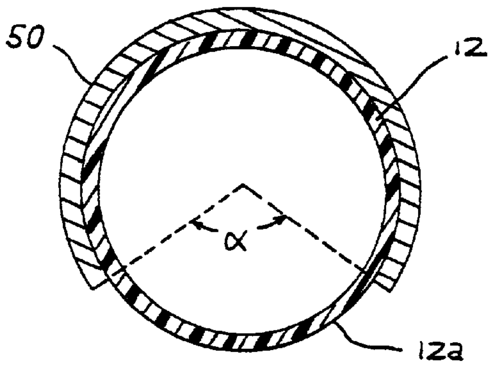
FIG. 6 is a view similar to FIG. 5 showing another version of a horizontal portion of the body of the blood access device.

FIG. 5 shows a cross section taken along line 5—5 in FIG. 2. In the embodiment shown in FIG. 5, the horizontal portion 22 covers the entire circumference of the artificial conduit 12. However, as shown in FIG. 6, the horizontal portion may be formed to cover only a part of the circumference of the artificial conduit 12. The horizontal portion 22 shown in FIG. 6 is arcuate-shaped in cross section, of which the lower part is cut out, so that the lower part of the artificial conduit 12 is exposed. The exposed part 12*a* of the artificial conduit 12 corresponds to their lower half at most. In other words, the angle α shown in FIG. 6 ranges from 0° to 180°. As described later in detail, both the body 10 and the artificial conduit 12 are placed in the human body of the patient. Therefore, according to the construction shown in FIG. 6, a feeling of physical discomfort which may tend to be caused when the rigid metallic body 10 comes into contact with the body tissue directly, is reduced.

Figure 9:
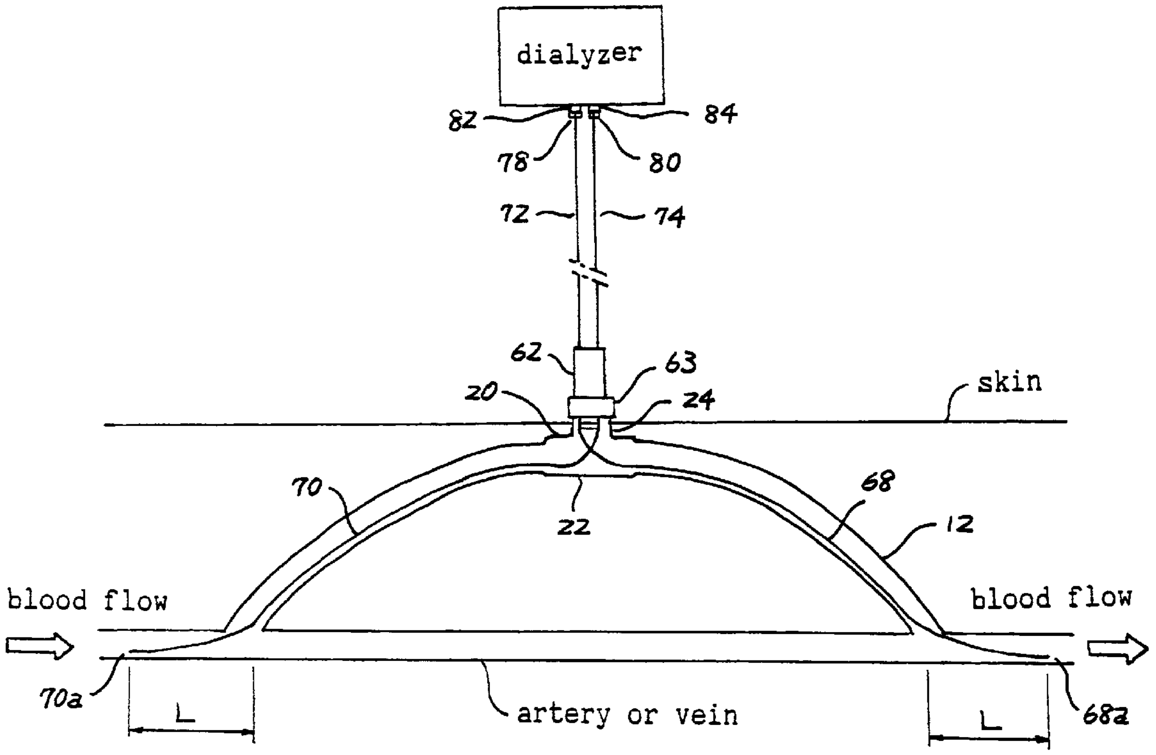
FIG. 9 is a diagrammatic view showing the condition wherein the no-needle blood access device and the no-needle connecting cannula assembly of the present invention are used to hemodialyze.
Figure 10:
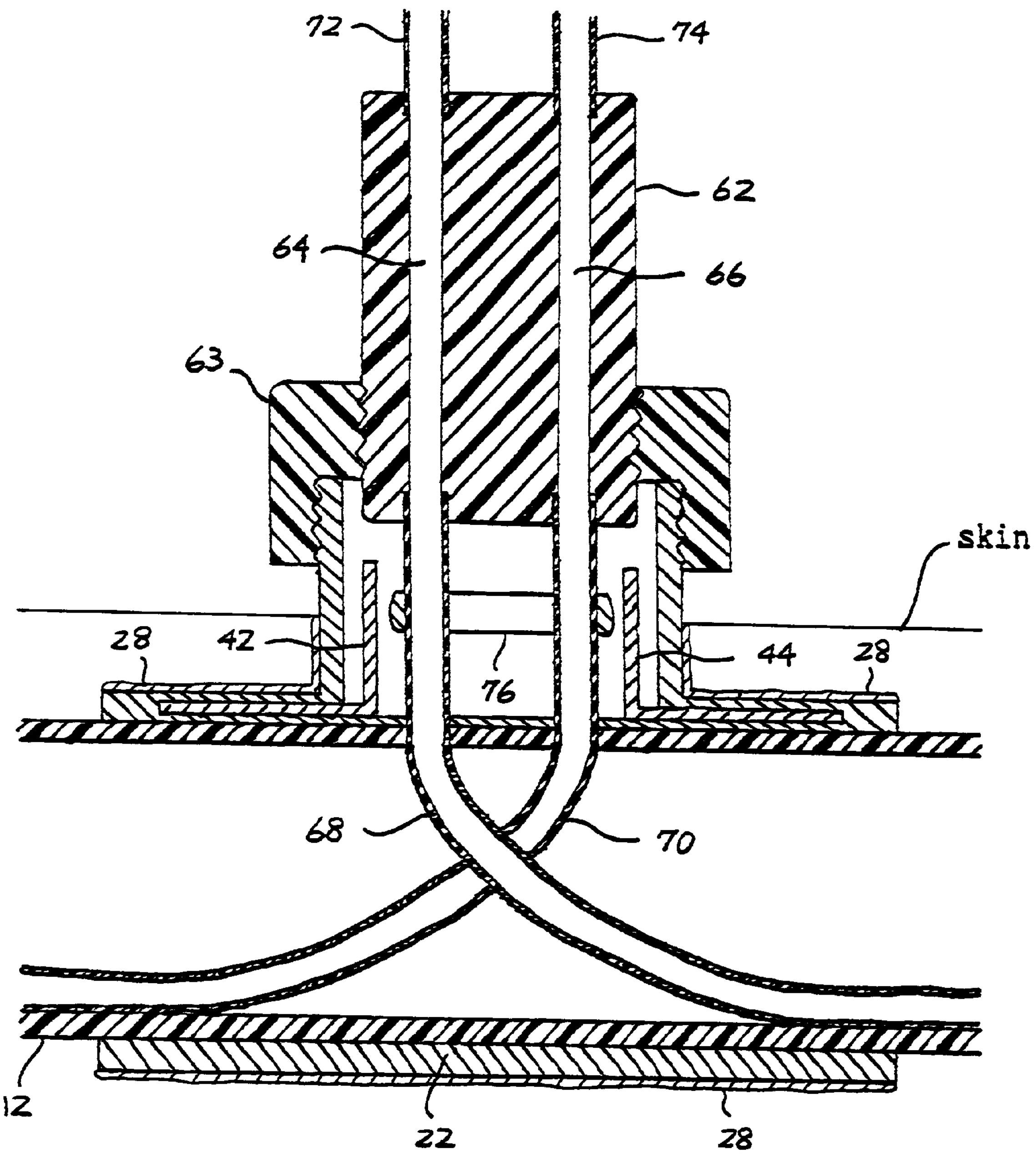
FIG. 10 is an enlarged sectional view of the body of the no-needle blood access device of FIG. 9.

A no-needle connecting cannula assembly for connecting the no-needle blood access device 10 to a dialyzer during hemodialysis will now be explained. A no-needle connecting cannula assembly generally indicated by a reference numeral 60 in FIG. 7A which is a first embodiment of the assembly of the present invention comprises a cap 62 provided with a pair of through-holes 64 and 66 (See FIG. 10 ), a first pair of cannulas 68 and 70 connected to one end of the through-holes 64 and 66 respectively so as to be in communication with the through-holes 64 and 66, and a second pair of cannulas 72 and 74 connected to the other end of the through-holes 64 and 66 respectively so as to be in communication with the through-holes 64 and 66, as best shown in FIG. 9. The cannulas 68, 70, 72 and 74 are made of a conventional flexible material, and the cap 62 is made of a plastic material.

The cap 62 is mounted with a box nut 63 for securing the body 20 of the blood access devices 10 to the cap 62 during hemodialysis, as described later.

Each of the cannulas 68 and 70 is a tube adapted to be inserted from the apertures 30 and 32 respectively through the artificial conduit 12 into the targeted artery or vein. The external diameter D2 of the respective leading ends 68*a* and 70*a* of the cannulas 68 and 70 (or, the respective ends opposite the side of the cannulas 68 and 70 to which the cap 62 is connected) is selected to be slightly smaller than the diameter D1 of the apertures 30 and 32 to facilitate the insertion of the cannulas 68 and 70 into the apertures 30 and 32 respectively. The external diameter D3 of the respective ends 68*b* and 70*b* of the side of the cannulas 68 and 70 to which the cap 62 is connected is selected to be slightly larger than the diameter D1 of the apertures 30 and 32 to avoid the leakage of blood during hemodialysis. From the foregoing, the relationship among the the diameters D1, D2 and D3 can be expressed as follows: $D2<D1<D3$.

Figure 7A:
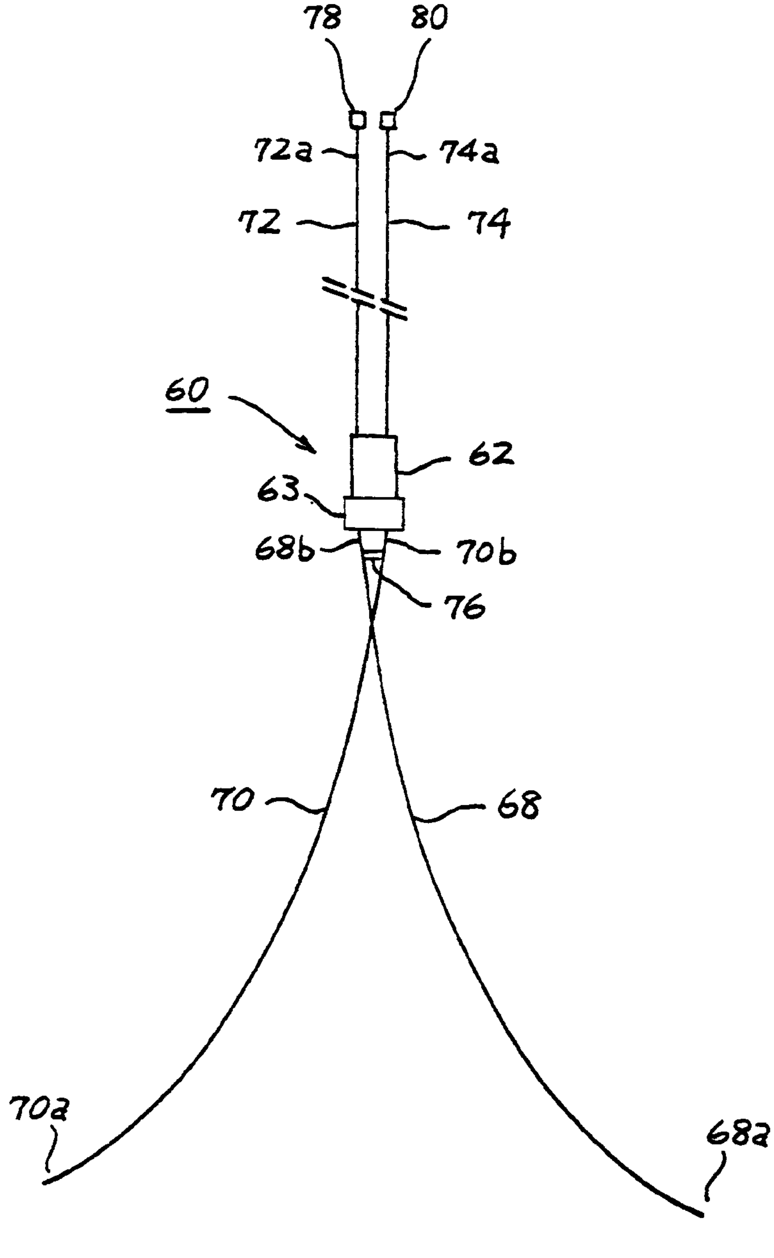
FIG. 7A is a diagrammatic view of a first embodiment of a no-needle connecting cannula assembly of the present invention.

As shown in FIG. 7A, the cannula 68 curves so that the curvature becomes larger from the end 68*b* towards the end 68*a*, and intersects at a location adjacent to the end 68*b*. The cannula 70 also curves so that the curvature becomes larger from the end 70*b* towards the end 70*a*, and intersects at a location adjacent to the end 70*b*. The cannulas 68 and 70 may be provided with a spacer member 76 for holding the spacing between the cannulas 68 and 70 at a location adjacent to the ends 68*b* and 70*b*. Thereby the insertion of the cannulas 68 and 70 into the artery or the vein can be effected smoothly.

The cannulas 72 and 74 are tubes adapted to define a connecting circuit leading to the dialyzer, and each of them has an internal diameter approximately equal to the internal diameter of each of the cannulas 68 and 70. The cannula 72 is provided at the end 72 proximal to the dialyzer with a terminal 78 for connecting to a terminal 82 of the dialyzer. The cannula 74 is also provided at the end 74*a* proximal to the dialyzer with a terminal 80 for connecting to a terminal 84 of the dialyzer. Each of the terminals 78 and 80 may be a conventional screw type terminal. Each of the cannulas 72 and 74 has a length (at least 3 meters) sufficient for the patient to move around with relative freedom during hemodialysis. Since the internal diameter of each of the cannulas 72 and 74 is selected to be approximately equal to that of each of the cannulas 68 and 70 as described above, the length of each of the cannulas 72 and 74 can be increased without increasing the amount of blood circulating outside the body of the patient.

Figure 8A:
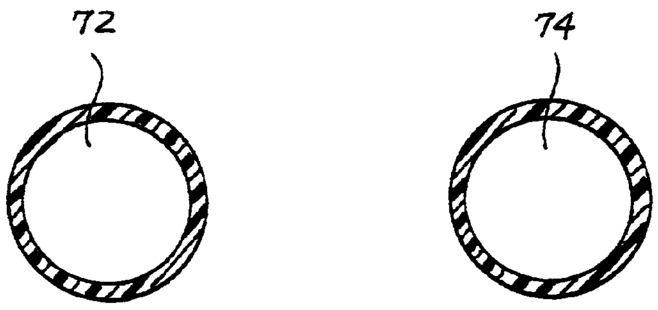
FIG. 8A is a cross sectional view showing a first pair of cannulas of the no-needle connecting cannula assembly of the present invention.
Figure 8B:
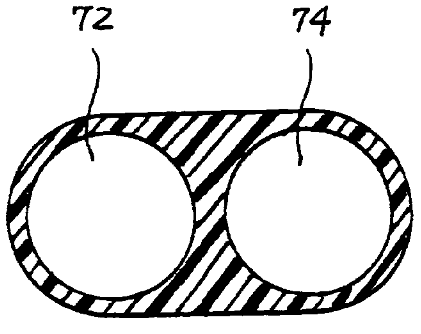
FIG. 8B is a cross sectional view showing another version of the first pair of cannulas of the no-needle connecting cannula assembly of the present invention.

The cannulas 72 and 74 may consist of either two separate tubes as shown in FIG. 8A, or one tube in appearance which is made by combining two tubes as shown in FIG. 8B.

A no-needle connecting cannula assembly generally indicated by a reference numeral 86 in FIG. 7B which is a second embodiment of the assembly of the present invention is substantially similar to the assembly 60 except that the cannulas 68 and 70 do not intersect at the location adjacent to the ends 68*b* and 70*b*.

Figure 7C:
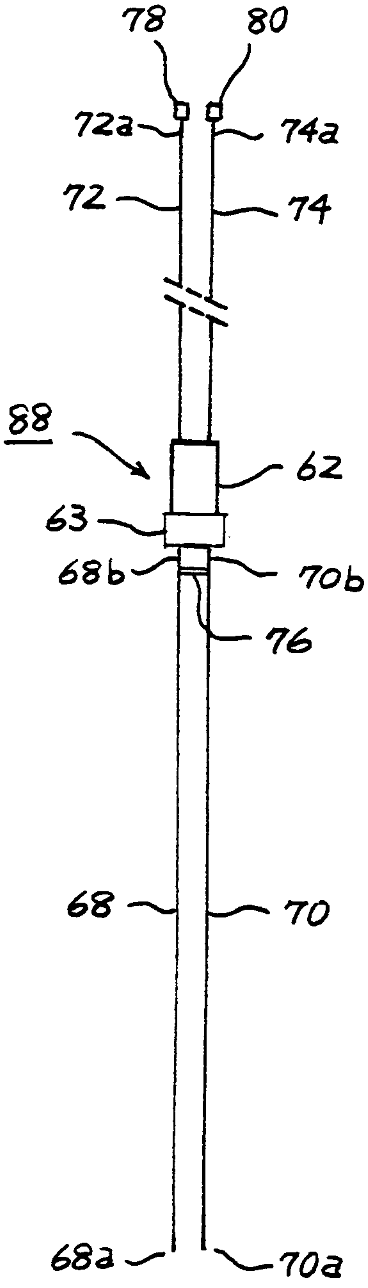
FIG. 7C is a diagrammatic view of a third embodiment of the no-needle connecting cannula assembly of the present invention.

Further, a no-needle connecting cannula assembly generally indicated by a reference numeral 88 in FIG. 7C which is a third embodiment of the assembly of the present invention is substantially similar to the assembly 60 except that each of the cannulas 68 and 70 do not curve.

The thus constituted no-needle blood access device for hemodialysis 10 and no-needle connecting cannula assembly 60 operates as follows. Firstly, as shown in FIG. 1, the body 20 is implanted in a desired area of the upper arm, etc, of the patient and the artificial conduit 12 is anastomosed to the targeted artery or vein. When it is to be hemodialyzed, the cap 48 is removed from the body 20, and then the clip 46 is taken off from the shutters 34 and 36 to open them by a tool such as a pincette. Thereafter, as shown in FIG. 9, each of the cannulas 68 and 70 of the no-needle connecting cannula assembly 60 which is connected to the dialyzer is inserted from the apertures 30 and 32 of the body 20 through the artificial conduit 12 into the targeted artery or vein respectively. Then, as shown in FIG. 9, it is desirable that the distance L between the anastomosis area of the artificial conduit 12 to the artery or vein and the respective leading ends 68*a* and 70*a* of the cannulas 68 and 70 is about 3 centimeters. It is necessary to tighten the box nut 63 to prevent the cap 62 from being removed from the body 20. When hemodialysis is completed, each of the cannulas 68 and 70 is withdrawn, and the shutters 34 and 36 are closed and secured by the clip 46, and then, the top of the vertical portion 24 is covered with the cap 48. The used assembly 60 may be discarded.

The present invention has thus been shown and described with reference to specific embodiments. However, it should be noted that the present invention is in no way limited to the details of the described arrangements but changes and modification may be made without departing from the scope of the appended claims.

For example, although the vertical portion of the body is shown as having a cylindrical shape in the above described embodiments, they may have other shapes. Further, although the artificial conduit is anastomosed to the same artery or vein in the above described embodiments, each end of the artificial conduit may be anastomosed to separate arterys or veins.

Further, the no-needle connecting cannula assembly 60 is explained in relation to its use together with the no-needle blood access device 10. However, the no-needle connecting cannula assembly 60 may be use with other types of external shunts.

According to the present invention, since the body has a simple structure, the blood access device for hemodialysis which does not require needle puncture and can be manufactured at a relatively low cost and is easy to handle, is provided. Further, by using the no-needle connecting cannula assembly of the present invention, the patient can move around with relative freedom during hemodialysis.

What is claimed is:

1. A no-needle blood access device for hemodialysis comprising, an artificial conduit whose opposite ends are adapted to be anastomosed to a target artery or vein;

a metallic body, the body including a cylindrical horizontal portion covering the entire circumference of the conduit or an arcuate-shaped horizontal portion covering at least an upper half of the circumference of the conduit, and a cylindrical vertical portion connected to approximately the center of an upper part of the horizontal portion so as to be disposed perpendicular to the horizontal portion, defining a well therein, and having one end adapted to project through the skin of a patient to make the well externally accessible, the horizontal portion being provided at a part located at the bottom of the well with a first pair of apertures, the conduit being provided at a corresponding part with a second pair of apertures, whereby the well is in communication with the conduit through each of the apertures; and a pair of shutters slidably housed within opposed pockets formed in the upper part of the horizontal portion and arranged such that the shutters are accessible in the well and can be opened and closed, wherein each of the shutters is provided at opposite ends with upwardly extending projection pieces, the projection pieces serving as a knob during opening and closing of the shutters, and wherein one of the projection pieces is formed to be higher than the other;

whereby the device is arranged such that, when the shutters are opened, the well is brought into communication with the conduit, and when the shutters are closed, the well is brought out of communication with the conduit.

2. A no-needle blood access device for hemodialysis comprising, an artificial conduit whose opposite ends are adapted to be anastomosed to a target artery or vein;

a metallic body, the body including a cylindrical horizontal portion covering the entire circumference of the conduit or an arcuate-shaped horizontal portion covering at least an upper half of the circumference of the conduit, and a cylindrical vertical portion connected to approximately the center of an upper part of the horizontal portion so as to be disposed perpendicular to the horizontal portion, defining a well therein, and having one end adapted to project through the skin of a patient to make the well externally accessible, the horizontal portion being provided at a part located at the bottom of the well with a first pair of apertures, the conduit being provided at a corresponding part with a second pair of apertures, whereby the well is in communication with the conduit through each of the apertures; and a pair of shutters slidably housed within opposed pockets formed in the upper part of the horizontal portion and arranged such that the shutters are accessible in the well and can be opened and closed, wherein each of the shutters is provided at opposite ends with upwardly extending projection pieces respectively, the projection pieces serving as a knob during opening and closing of the shutters, and wherein each of the projection pieces is mounted on the shutters respectively so that one of the projection pieces shifts slightly with respect to the other in a horizontal direction;

whereby the device is arranged such that, when the shutters are opened, the well is brought into communication with the conduit, and when the shutters are closed, the well is brought out of communication with the conduit.

3. A no-needle blood access device for hemodialysis comprising, an artificial conduit whose opposite ends are adapted to be anastomosed to a target artery or vein;

a metallic body, the body including a cylindrical horizontal portion covering the entire circumference of the conduit or an arcuate-shaped horizontal portion covering at least an upper half of the circumference of the conduit, and a cylindrical vertical portion connected to approximately the center of an upper part of the horizontal portion so as to be disposed perpendicular to the horizontal portion, defining a well therein, and having one end adapted to project through the skin of a patient to make the well externally accessible, the horizontal portion being provided at a part located at the bottom of the well with a first pair of apertures, the conduit being provided at a corresponding part with a second pair of apertures, whereby the well is in communication with the conduit through each of the apertures; and a pair of shutters slidably housed within opposed pockets formed in the upper part of the horizontal portion the shutters are accessible in the well and can be opened and closed, an end of the first shutter facing the second shutter is provided with a recess or a stepped part, and an end of the second shutter facing the first shutter is provided with a projection or a stepped part adapted to mate with the recess or the stepped part when the shutters are closed;

whereby the device is arranged such that, when the shutters are opened, the well is brought into communication with the conduit, and when the shutters are closed, the well is brought out of communication with the conduit.

4. A no-needle blood access device for hemodialysis comprising, an artificial conduit whose opposite ends are adapted to be anastomosed to a target artery or vein;

a metallic body, the body including a cylindrical horizontal portion covering the entire circumference of the conduit or an arcuate-shaped horizontal portion covering at least an upper half of the circumference of the conduit, and a cylindrical vertical portion connected to approximately the center of an upper part of the horizontal portion so as to be disposed perpendicular to the horizontal portion, defining a well therein, and having one end adapted to project through the skin of a patient to make the well externally accessible, the horizontal portion being provided at a part located at the bottom of the well with a first pair of apertures, the conduit being provided at a corresponding part with a second pair of apertures, whereby the well is in communication with the conduit through each of the apertures; and a pair of shutters slidably housed within opposed pockets formed in the upper part of the horizontal portion respectively and arranged such that they are accessible in the well and can be opened and closed, wherein each of the shutters is provided at opposite ends with upwardly extending projection pieces, the projection pieces serving as a knob during opening and closing of the shutters, and wherein an end of the first shutter facing the second shutter is provided with a recess or a stepped part, and an end of the second shutter facing the first shutter is provided with a projection or a stepped part adapted to mate with the recess or the stepped part of the first shutter when the shutters are closed;

whereby the device is arranged such that, when the shutters are opened, the well is brought into communication with the conduit, and when the shutters are closed, the well is brought out of communication with the conduit.

5. A no-needle blood access device for hemodialysis in accordance with claim 1, wherein an end of the first shutter facing the second shutter is provided with a recess or a stepped part, and an end of the second shutter facing the first shutter is provided with a projection or a stepped part adapted to mate with the recess or the stepped part of the first shutter when the shutters are closed.

6. A no-needle blood access device for hemodialysis in accordance with claim 2, wherein an end of the first shutter facing the second shutter is provided with a recess or a stepped part, and an end of the second shutter facing the first shutter is provided with a projection or a stepped part adapted to mate with the recess or the stepped part of the first shutter when the shutters are closed.

7. A no-needle connecting cannula assembly for hemodialysis comprising, a cap provided with a pair of through-holes;

a first pair of cannulas connected to one end of the pair of through-holes so as to be in communication with the corresponding through-holes, an external diameter of respective leading ends of the cannulas being selected to be slightly smaller than that of apertures defined within a body of a no-needle blood access device used in conjunction with the cannula assembly, an external diameter of the respective ends of the side of the cannulas to which the cap is connected being selected to be slightly larger than the diameter of the apertures defined within the body of the no-needle access device; and a second pair of cannulas connected to an opposing end of the pair of through-holes so as to be in communication with the corresponding through-holes and adapted to define a connecting circuit leading to a dialyzer, the second pair of cannulas having an internal diameter approximately equal to an internal diameter of each of the first pair of cannulas, the second pair of cannulas having at least 3 meters in length, one of the second pair of cannulas being provided at an end proximal to the dialyzer with a terminal for connecting to a terminal of the dialyzer, the other of the second paid of cannulas being provided at an end proximal to the dialyzer with a terminal for connecting to a terminal of the dialyzer.

8. A no-needle connecting cannula assembly in accordance with claim 7, wherein the first pair of cannulas curve so that the curvature becomes larger from the end proximal to the cap towards an end distal to the cap.

9. A no-needle connecting cannula assembly for hemodialysis comprising, a cap provided with a pair of through-holes;

a first pair of cannulas connected to one end of the pair of through-holes respectively so as to be in communication with the corresponding through-holes, an external diameter of the respective leading ends of the cannulas being selected to be slightly smaller than that of apertures defined within a body of a no-needle blood access device used in conjunction with the cannula assembly, an external diameter of the respective ends of the side of the cannulas to which the cap is connected being selected to be slightly larger than the diameter of the apertures;

a second pair of cannulas connected to an opposing end of the pair of through-holes so as to be in communication with the corresponding through-holes and adapted to define a connecting circuit leading to a dialyzer, the second pair of cannulas having an internal diameter approximately equal to an internal diameter of each of the first pair of cannulas, the second pair of cannulas having at least 3 meters in length, one of the second pair of cannulas being provided at an end proximal to the dialyzer with a terminal for connecting to a terminal of the dialyzer, the other of the second paid of cannulas being provided at an end proximal to the dialyzer with a terminal for connecting to a terminal of the dialyzer; and wherein, the first pair of cannulas curve so that the curvature becomes larger from the end proximal to the cap towards the end distal to the cap and intersects at a location adjacent to an end proximal to the cap.

10. A no-needle connecting cannula assembly for hemodialysis comprising, a cap provided with a pair of through-holes;

a first pair of cannulas connected to one end of the pair of through-holes respectively so as to be in communication with the corresponding through-holes, an external diameter of the respective leading ends of the cannulas being selected to be slightly smaller than that of apertures defined within a body of a no-needle blood access device used in conjunction with the cannula assembly, an external diameter of the respective ends of the side of the cannulas to which the cap is connected being selected to be slightly larger than the diameter of the apertures defined within the body of the no-needle access device;

a second pair of cannulas connected to an opposing end of the pair of through-holes so as to be in communication with the corresponding through-holes and adapted to define a connecting circuit leading to a dialyzer, the second pair of cannulas having an internal diameter approximately equal to an internal diameter of each of the first pair of cannulas, the second pair of cannulas having at least 3 meters in length, one of the second pair of cannulas being provided at an end proximal to the dialyzer with a terminal for connecting to a terminal of the dialyzer, the other of the second paid of cannulas being provided at an end proximal to the dialyzer with a terminal for connecting to a terminal of the dialyzer; and wherein, when each of the first pair of cannulas is inserted from the apertures of the body of the no-needle blood access device for hemodialysis through an artificial conduit into a targeted artery or vein, each of the first pair of cannulas having a length which is selected so that a distance between an anastomosis area of the artificial conduit to the targeted artery or vein and the respective leading ends of the first pair of cannulas is about 3 centimeters.

11. A no-needle connecting cannula assembly for hemodialysis comprising, a cap provided with a pair of through-holes;

a first pair of cannulas connected to one end of the pair of through-holes so as to be in communication with the corresponding through-holes, an external diameter of the respective leading ends of the cannulas being selected to be slightly smaller than that of apertures defined within a body of a no-needle blood access device used in conjunction with the cannula assembly, an external diameter of the respective ends of the side of the cannulas to which the cap is connected being selected to be slightly larger than the diameter of the apertures defined within the body of the no-needle access device;

a second pair of cannulas connected to an opposing end of the pair of through-holes so as to be in communication with the corresponding through-holes and adapted to define a connecting circuit leading to a dialyzer, the second pair of cannulas having an internal diameter approximately equal to an internal diameter of each of the first pair of cannulas, the second pair of cannulas having at least 3 meters in length, one of the second pair of cannulas being provided at an end proximal to the dialyzer with a terminal for connecting to a terminal of the dialyzer, the other of the second paid of cannulas being provided at an end proximal to the dialyzer with a terminal for connecting to a terminal of the dialyzer;

wherein the first pair of cannulas curve so that the curvature becomes larger from an end proximal to the cap towards an end distal to the cap; and wherein, when each of the first pair of cannulas is inserted from the apertures of the body of the no-needle blood access device for hemodialysis through an artificial conduit into a targeted artery or vein, each of the first pair of cannulas having a length which is selected so that a distance between an anastomosis area of the artificial conduit to the targeted artery or vein and the respective leading ends of the first pair of cannulas is about 3 centimeters.

12. A no-needle connecting cannula assembly in accordance with claim 9, wherein, when each of the first pair of cannulas is inserted from the apertures of the body of the no-needle blood access device for hemodialysis through an artificial conduit into a targeted artery or vein, each of the first pair of cannulas having a length which is selected so that a distance between an anastomosis area of the artificial conduit to the targeted artery or vein and the respective leading ends of the first pair of cannulas is about 3 centimeters.

* * * * *